United States Patent [19]
Nelson

[11] Patent Number: 4,963,256
[45] Date of Patent: Oct. 16, 1990

[54] DIALYSIS CELL

[75] Inventor: Jerald C. Nelson, Corona del Mar, Calif.

[73] Assignee: Nichols Institute Diagnostics, San Juan Capistrano, Calif.

[21] Appl. No.: 210,859

[22] Filed: Jun. 24, 1988

Related U.S. Application Data

[63] Continuation of Ser. No. 750,670, Jul. 2, 1985, abandoned, which is a continuation-in-part of Ser. No. 627,894, Jul. 5, 1984, abandoned.

[51] Int. Cl.$^5$ .............................................. B01D 61/28
[52] U.S. Cl. .................... 210/232; 210/321.6; 210/482
[58] Field of Search ............... 210/232, 645, 644, 482, 210/321.6; 530/354, 387; 424/101; 252/408.1

[56] References Cited

U.S. PATENT DOCUMENTS

| | | | |
|---|---|---|---|
| 1,578,903 | 3/1926 | McGowan | 210/482 X |
| 2,692,854 | 10/1954 | Henley | 210/8.5 |
| 2,985,587 | 5/1961 | Hoch et al. | 210/644 X |
| 3,108,066 | 10/1967 | Chantooni | 210/321 |
| 3,702,820 | 11/1972 | Hough | 210/644 X |
| 3,830,106 | 8/1974 | Gardiner | 210/321.2 X |
| 3,917,119 | 11/1975 | Kahn | 222/108 |
| 4,077,875 | 3/1978 | Kremer | 210/23 F |
| 4,108,975 | 8/1978 | Hales | 424/1 |
| 4,113,433 | 9/1978 | Khare | 23/230.6 |
| 4,115,539 | 9/1978 | Eisenhardt, Jr. et al. | 424/1 |
| 4,155,711 | 5/1979 | Zelagin et al. | 23/230.6 |
| 4,196,085 | 4/1980 | Saravis | 210/34.2 X |
| 4,240,912 | 12/1980 | Stumpf et al. | 210/321.2 |
| 4,296,203 | 10/1981 | Verma | 435/240 |

OTHER PUBLICATIONS

Wang, Y., Hershman, J. M., and Pekary, A. E., Clinical Chemistry, vol. 31, No. 4 (1985) pp. 517–522.
Ekins, R. P. and Ellis, S. M., "The Radioimmunoassay of Free Thyroid Hormones in Serum", pp. 597–600.
Lee, N. D. and Pileggi, V. J., Clinical Chemistry, vol. 17, No. 3 (1971), pp. 166–173.
Helenius, T. and Liewendahl, K., Clinical Chemistry, vol. 29, No. 5, (1983), pp. 816–822.

Primary Examiner—Frank Spear
Attorney, Agent, or Firm—Saidman, Sterne, Kessler & Goldstein

[57] ABSTRACT

A sampling device for use with an open necked container capable of holding a fluid material, comprises a hollow support member insertable into the container through the open necked portion thereof. The support member comprises a main body portion of a smaller diameter than the open neck of the container; a first end portion extends from the main body portion and is open to the ambient atmosphere through the open neck portion of the container. In one embodiment, elongated ribbed members extend from the main body portion and define a second end portion. The ribbed members form a generally rigid support structure. A dialysis tubing is fitted over the ribbed members and is closed at one end to define an open ended dialysis sac, the inside of which is directly accessible through the first end portion of the support structure.

19 Claims, 2 Drawing Sheets

FIG. 6

DIALYSIS CELL

CROSS REFERENCE TO RELATED APPLICATION

This application is a continuation of application Ser. No. 750,670, filed July 2, 1985, which is a continuation-in-part of Ser. No. 627,894, filed July 5, 1984, both now abandoned.

BACKGROUND OF THE INVENTION

This invention relates to dialysis cells. More particularly, the invention relates to a disposable cell that is economical to manufacture and easy to use.

There has been an effort over the last 10 years to develop for clinical and clinical research laboratories some method of estimating free hormone concentrations other than by measuring them indirectly. Equilibrium dialysis is regarded as the best method of separating protein-bound ligand from free ligand, and is used particularly in the thyroid field where iodinated tracers are used. However, it is considered to be a cumbersome procedure, difficult to do, and entirely outside the purview of routine clinical chemistry.

Two factors have contributed to this. One is that there is a mystique about how to measure the dialyzable fraction of thyroxine, which involves equilibrium dialysis of serum to which a tracer amount of radioiodine labelled thyroxine has been added. That mystique is, in part, due to a less than fully understood de-iodination of thyroxine that occurs immediately after its preparation. If a laboratory were to buy radio-iodine labelled thyroxine from a company that sells radio nuclides, by the time the shipment got to the laboratory, the product would be contaminated with radio-iodides and some radio-iodine labelled thyroxines. There are methods available for repurifying that material in the laboratory just before its use; however, during the incubation (which is necessary to achieve equilibrium), further de-iodination occurs, so that the dialysate radioactivity is always made up of at least two molecular species: radio-iodide, which may have been generated during the dialysis incubation, and the radio-iodine labelled thyroxine. The relationship of the one molecular species to the other varies depending on the clinical state of the patient from whom the serum is taken.

With respect to the dialysis itself, published studies indicate that it is important to hold the chemical composition of the serum during dialysis at a physiologic constant. In an effort to get around this iodide contamination problem, and because iodide is not found in serum proteins, almost all dialysis chemistries previously devised for the measurement of free hormones, including thyroxine, employ simple buffers that radically distort the ionic environment of the serum proteins and dilute the serum proteins. As a result, one cannot obtain an accurate measurement of, for example, the dialyzable free thyroxine fraction using undiluted serum samples, unless a large dialysate volume is used to dilute out the iodide.

Standard methods for the measurement of free thyroxine in serum involve dialysis to separate the free form from the protein-bound form. The partitioning of thyroxine between the free and bound forms is estimated by the addition of radioiodine-labeled thyroxine to the serum sample prior to dialysis. The dialysis is carried out by using a diluted serum sample and/or a great excess of dialysate volume to assist in controlling pH (which has a profound effect on $T_4$ binding to serum proteins) and to help in minimizing the effect of contaminating iodide which poses a major methodologic difficulty. Direct radioimmunoassays of $T_4$ in serum dialysates in an effort to avoid the tracer $T_4$ induced artifact resulting from spontaneous deiodination and radioiodide contamination of tracer $T_4$ have been described previously.

It has now been discovered that the rate of tracer $T_4$ deiodination during the equilibrium dialysis incubation is different for different sera and that radioiodide contamination of tracer $T_4$ is different in the dialysates of different sera. It has also been discovered that the effect of diluting serum proteins is different on sera from different clinical disorders.

It is clear that it would be desirable to measure free $T_4$ concentrations by a method which distorts the endogenous environment as little as possible. Such a method would employ a direct measurement of free $T_4$ by radioimmunoassay and avoid the addition of radioiodine-labeled $T_4$ tracers. Furthermore, it would dilute the serum sample as little as possible, employ a buffer which is as much like an ultrafiltrate of serum as is possible and carry out the dialysis procedure not only at physiologic temperatures but also in an environment of gases which mimic the physiologic in vivo situation.

In one of its embodiments, the dialysis cell of this invention is designed to accomplish this by allowing the dialysis of a small volume of buffer against a large volume of serum sample in an atmosphere containing physiologic concentrations of blood gases. At the completion of dialysis the dialysate sample for radioimmunoassay quantification can be volumetrically pipetted from the dialysis cell into the RIA tube and the dialysis cell can be discarded.

The following references contain disclosure with respect to dialysis cells: Helenius, T. and Liewendahl, K., "Improved Dialysis Method for Free Thyroxin in Serum Compared with Five Commercial Radioimmunoassays in Nonthyroidal Illness and Subjects with Abnormal Concentrations of Thyroxin-Binding Globulin," *Clinical Chemistry*, Vol. 29, No. 5, (1983), pages 816–822; Lee, N. D. and Pileggi, V. J., "Measurement of 'Free' Thyroxine in Serum," *Clinical Chemistry*, Vol. 17, No. 3, (1971), pages 166–173; and Elkins, R. P. and Ellis, S. M., "The Radioimmunoassay of Free Thyroid Hormones in Serum" (Excerpta Medica, 7th International Thyroid Conference, Abstract #158 (1976)), pages 597–600; Weeke, J., & Orskov, J., *Recent Advances in Clinical Biochemistry* (Churchill-Livingston: Edinburgh, N.Y. (1978)), pages 111–128; U.S. Pat. No. 4,077,875 to Kremer issued Mar. 7, 1978.

The dialysis cell described by Helenius et al. has an upper compartment and a lower compartment rather than inner and outer compartments. In assembling that cell any air included in the lower compartment would rise to the membrane and interfere with diffusion of dialyzable substances. The Helenius et al. cell must be assembled with a rubber ring to attach the dialysis membrane to the upper compartment and an aluminum clamping device with two screws to hold the upper and lower compartments tightly together. This cell is not disposable and must be washed and rinsed thoroughly before reuse.

The Ekins et al. cell also consists of an upper compartment and a lower compartment, which raises the problem of trapped air beneath the dialysis membrane that would impede dialysis. In the Ekins et al. cell, the lower compartment is filled with dialysate; then a membrane is stretched across the lower compartment and pressed into the lower compartment by an intermediate unit which contains the serum sample. This in turn is capped by a screw-capped top that closes the entire chamber. This cell is not opened to the environmental air for gas exchange, it is more difficult to assemble, and it is not made of disposable material.

The Lee et al. cell is currently widely used for equilibrium dialysis. It consists of two acrylic plastic halves each of which contains a cut out cavity of matching size as well as holes through which bolts can be placed to attach each half to the other. A dialysis membrane is placed between the halves, the bolts and nuts are tightened (a step which is critical since leaking will cause errors) and the sample is introduced through a narrow port on one side and the buffer through a similar port on the other side. This chamber is expensive and not disposable. It requires considerable effort to wash and prepare the chamber prior to utilization and between assay runs. Furthermore, the ports are too small to allow equilibration with ambient gases or sampling with common quantitative hand-held pipettors.

The dialysis cell illustrated by Weeke et al. consists of dialysis tubing supported in a test tube with a stopper on top of the tube supporting the tubing and closing its two ends. This creates an inner and outer compartment but leaves both blocked from the ambient atmosphere and makes sampling of the inner compartment difficult. Furthermore, the handicraft required to handle wet dialysis tubing, introduce a sample or buffer into the tubing without loss and close both ends after suspending the tubing in the test tube and surrounding it with the test tube contents is a matter of considerable skill.

The Kremer cell is designed to spread the inner compartment contents in a thin layer against the dialysis membrane by filling most of this compartment with solid material. The equipment is non-disposable, and complex to assemble, disassemble, wash and prepare for reuse.

SUMMARY OF THE INVENTION

In one of its embodiments, the dialysis cell of this invention includes a vial for containing a first fluid and having an open end or mouth portion. A disposable dialysis chamber fits into the vial through the open end portion; the dialysis chamber comprises an elongated hollow member for containing a second fluid. The hollow member is open at one end to permit open communication between the interior of the hollow member and the ambient atmosphere. The walls of the hollow member are composed of a substantially rigid, fluid impervious material. Elongated slotted openings are defined between spaced apart rib portions formed in the hollow member and provide a communication path between the interior of the hollow member and a medium contained in the vial when the hollow member is inserted into the vial. A dialysis membrane is supported on and by the rib portions of the hollow member in the communication path between the medium contained in the vial and the interior of the hollow member.

In another of its aspects, the dialysis cell comprises a first fluid-containing compartment effectively sealed from exposure to ambient conditions, and a second fluid-containing compartment having walls defining a first opening which allows communications between the first and second compartments and a second opening which allows open communication between the second compartment and ambient conditions. A semipermeable membrane of a polycellulose material covers the first opening and seals the membrane to the second compartment walls in a fluid tight manner to substantially effectively prevent transfer of fluids between the compartments except through the membrane. The second compartment is so shaped that evaporative loss of a given fluid from the second compartment through the second opening is substantially equal to osmotic gain of the given fluid from the first compartment into the second compartment through the membrane. The membrane seal preferably is itself sealed off from communication with the first and second compartments.

DESCRIPTION OF THE PREFERRED EMBODIMENTS

The several embodiments of the dialysis cell of the present invention are described in detail below with reference to the accompanying drawing figures.

In one embodiment, the dialysis cell comprises a chamber, generally designated 10, preferably made of a rigid or semi-rigid plastic housing, and a vial 26. The chamber 10 is composed of a cylindrical side wall portion 12. Support ribs 14 extend from side wall portion 12. Slots 16 are defined between ribs 14. In one version, shown in FIG. 1, the chamber 10 has an enlarged diameter side wall portion 18 extending from side wall 12 remote from ribs 14 and slots 16. A ridge 20 is defined between the smaller and larger diameter side wall portions 12 and 18, respectively. Chamber 10 has an open top 22. A dialysis tubing 24 (of any known type) is slipped over the ribs 14 and at least a portion of side wall 12. The dialysis tubing is sealed at the bottom 25 of chamber 10 and around side wall 12 to form a dialysis sac.

Figure 1:
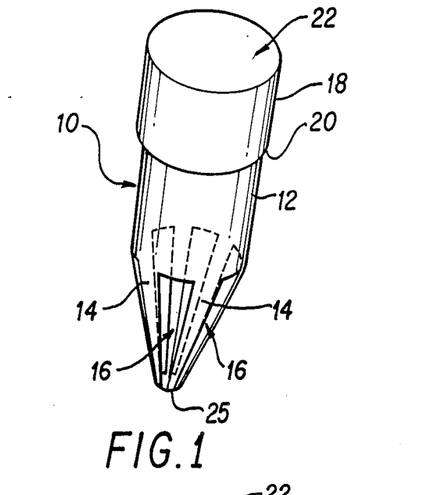
FIG. 1 shows a first embodiment of the dialysis chamber of the dialysis cell of this invention.
Figure 2:
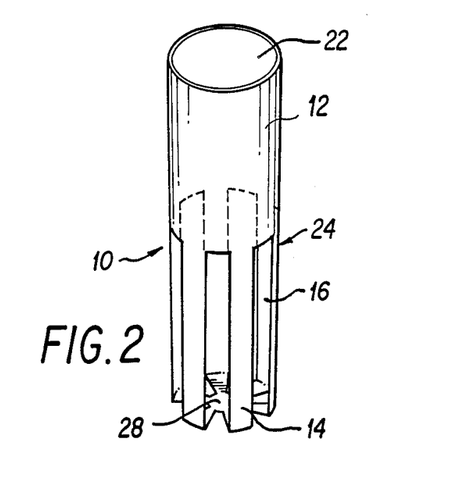
FIG. 2 shows a second embodiment of the dialysis chamber.

As shown in FIG. 1, the rib portions 14 taper inwardly toward their end points to define a conically shaped tubing support. In an alternate version, shown in FIG. 2, the ribs continue the cylindrical shape of side wall portion 12 (i.e., with essentially no tapering of the ribs 14). If additional support is desired, the ribs may terminate at a bottom plate 28 that may itself be slotted to continue the slots 16 (as shown in FIG. 2). Alternately, bottom plate 28 may be solid all the way across to add additional rigidity to the structure.

The dialysis chamber 10 may then be placed into a vial 26 with the top portion, including the open top 22, extending out of the top of the vial 26. The dialysis cell is thus divided into an inner compartment 32 and an outer compartment 34; dialysis tubing or membrane 24 provides a selective barrier between the two compartments.

Figure 3:
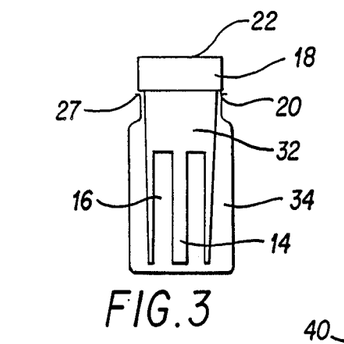
FIG. 3 shows a first embodiment of the complete dialysis cell.
Figure 4:
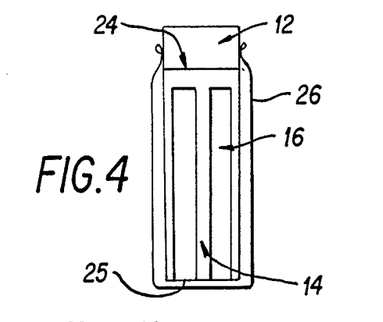
FIG. 4 shows a second embodiment of the complete dialysis cell.

FIG. 3 shows a modified version of the straight ribbed chamber of FIG. 2 with a larger diameter top portion 18 like that shown in FIG. 1. As shown in FIG. 3, the ridge 20 rests on the lip 27 of the open mouth of vial 26. When the mouth of the vial 26 is the same size as (or slightly smaller than) the outside of the cylinder 12, the vial holds the chamber 10 in place, as shown in FIG. 4. When the mouth of the vial is larger than the cylinder 12 a vial cap 36 may be added which has a central hole 38 into which the cylinder 12 fits snugly.

Figure 5:
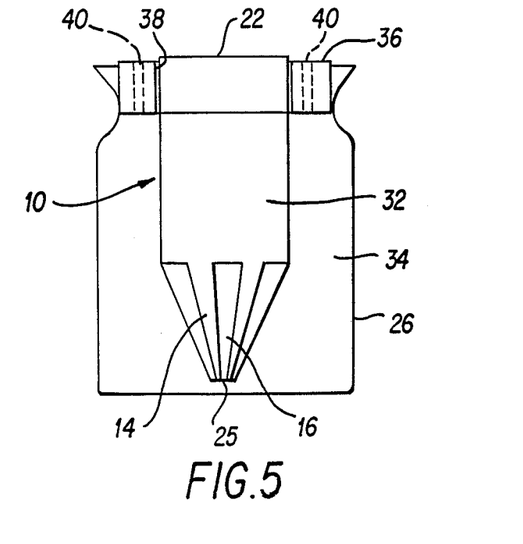
FIG. 5 shows a straight-sided dialysis chamber with a conically shaped tubing support mounted in a vial with a modified vial cap.

When ventilation of the inner compartment for equilibration with ambient gases (e.g. $CO_2$) is desired, the open end 22 of the chamber 10 is uncovered. When direct ventilation of the outer compartment 34 is also desired, a larger vial 26 is used and the cap 38 used to support the dialysis chamber contains ventilation ports 40, as shown in FIG. 5. The open end 22 of the chamber 10 and the openings 40 of the vial cap 38 can be also used for direct access to the inner or outer compartments for reagent or sample addition and removal. Typically, the inner compartment volume of the dialysis cell can vary from 150 ul to 5 ml and the outer compartment volume from 1 ml to 6 ml. This allows a wide range of applications which are not possible with existing cells.

The dialysis cell is designed to allow the dialysis of a small volume of a buffer liquid against a large volume of a serum sample (preferably in an atmosphere containing physiologic concentrations of blood gases). The dialysis chamber 10 is fitted into vial 26 which contains the serum sample so that the lower portion of the dialysis sac is immersed in the serum sample. The dialysis sac initially contains a buffer agent; the dialysis tubing or membrane 24 permits osmosis to occur, with high concentrations of materials (such as free thyroxine) in the serum migrating into the buffer in the dialysis sac until equilibrium is reached. At the completion of dialysis, the dialysate sample can be removed and analyzed. The dialysis chamber 10 and vial 26 are advantageously disposable and can be discarded after use.

When the fluid in the vial 26 is at a higher level than the fluid in the dialysis sac, a portion of the outer compartment contents is disposed next to the part of the dialysis membrane which has air as opposed to fluid on the other side. Evaporation occurs in the ambient atmosphere at the site of this membrane interface between the air and the vial fluid. When serum is placed in the vial and the vial is filled above the level of the sac, the water vapor loss can be balanced with the osmotic water gain due to the serum protein concentration. This leads to a net zero increase in serum water and maintenance of in vivo serum protein concentrations. This is a feature of the present invention which has not been described in other known dialysis systems.

Finally, upon completion of the dialysis, the disposable dialysis chamber 10 can be removed and the vial 26 capped to preserve the serum sample for storage and subsequent testing.

In summary, the above-described embodiments of the present invention have the following features.

The serum sample is placed in a standard specimen vial.

A hollow disposable dialysis chamber 10 which is open at the top is slipped into vial 26 and immersed in the serum, thereby creating a dialysis cell having an outer dialysis compartment containing the serum and an empty inner dialysis compartment or sac to which buffer can be added.

The dialysis chamber can be filled with dialysate buffer through the open top 22 of the dialysis chamber.

When dialysis is completed the buffer can be removed quantitatively by a hand-held pipettor for analysis, the dialysis chamber may be removed from the vial and discarded and the vial may be capped for serum storage.

The open end of the dialysis chamber allows rapid equilibration of dissolved gases with the gas environment (e.g. 5% $CO_2$ for pH control of serum or bicarbonate buffers) and easy access with hand held pipettors for quantitative sampling.

The ratio of inner compartment volume to outer compartment volume can be changed simply by using vials of different size.

There are no screws, clamps, nuts or bolts to tighten.

The two compartments of the dialysis cell are held in place by gravity and/or friction.

Since all parts are disposable there is no washing of used chambers for re-use.

Figure 6:
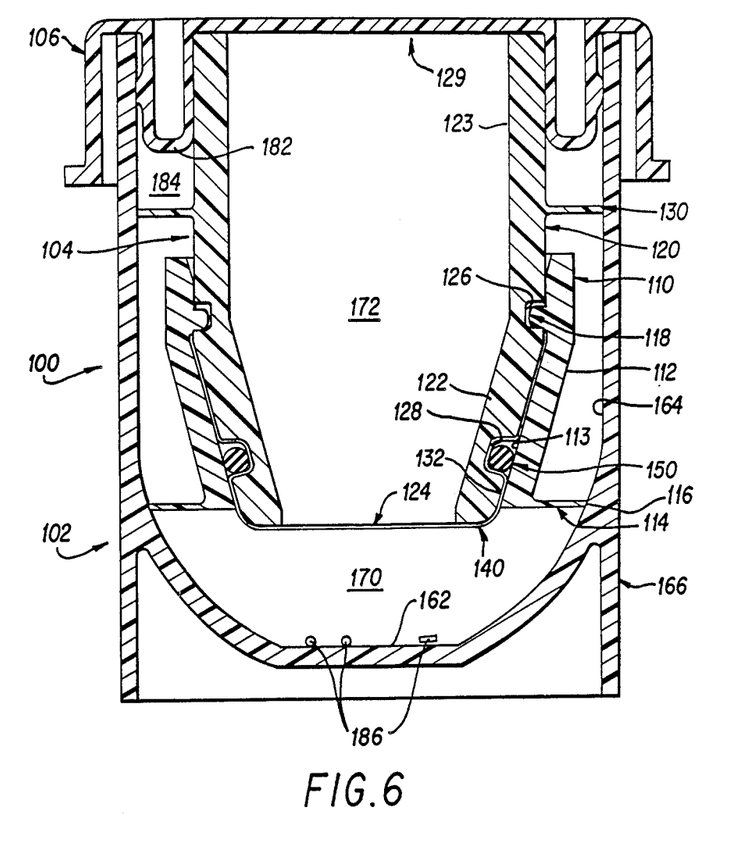
FIG. 6 shows a cross-sectional view of a further embodiment of the dialysis cell of this invention.

A further preferred embodiment of the invention is shown in FIG. 6. In this preferred embodiment, the dialysis cell is cylindrical. Other shapes, of course, may be used without departing from the scope of the invention.

In this embodiment, the cell 100 comprises a disposable vial 102 and a membrane cylinder, generally designated 104. A removable cap 106 is snap fitted over the membrane cylinder 104 and over the vial 102.

The membrane cylinder 104 includes an outer cylinder or hollow member 110 having a conical side wall portion 112 which tapers to an open end portion 114. A first seal member 116 extends laterally outwardly from the outer surface of cylinder 110. A protuberance 118 extends inwardly from the inner wall surface of cylinder 110; the purpose and function of protuberance 118 will be described in more detail below. The membrane cylinder 104 further comprises an inner cylinder or hollow member 120 having a conical wall portion 122 complementary to conical wall portion 112, which tapers to an open end 124, and a straight wall portion 123 extending from the widest portion of the conical wall section 122. As shown in FIG. 6, end portion 124 preferably extends beyond end portion 114 of outer cylinder 110. The outer wall surface of inner cylinder 120 has circumferential grooves 126 and 128 formed therein. A second seal member 130 extends laterally outwardly from the outer surface of cylinder 120. The straight sided wall section 123 terminates in an open end portion 129.

The seals 116 and 130 are preferably of a type marketed by V-Tech, Inc. of Los Angeles, Calif., under the name "Click-Stick." The opening 124 in cylinder 120 is sealed by a semi-permeable dialysis membrane 140. The membrane 140 is preferably made of a polycellulose material of known type. The membrane 140 is stretched over the open end 124 and is pressed over the outer surface of at least part of the conical wall portion 122. The membrane extends far enough up the side of conical wall 122 so that it may be pressed or entrained into recess 128. A compressible O ring sealing member 150 is fitted into groove 128 over the membrane 140. Typically, dialysis membranes are relatively stiff and it is difficult to form a fluid tight seal with them. One purpose of the compressible O-ring 150 is to mold itself to the very small ridges and channels formed in the membrane when the membrane is pressed into the groove 128. By forming itself to these micro-channels and ridges, the O-ring can effectively sandwich or compress the membrane against the wall surfaces of channel 128 to provide a fluid tight seal.

The cylinders 110 and 120 are press-fit over one another around the membrane 140 to form a "cone seal" between them. The inner diameter of the conical portion of cylinder 110 is greater than the outer diameter of the conical portion of cylinder 120. To ensure that the cylinders remain securely locked together, the protuberance 118 seats in or mates with groove 126 to provide a snap-fit lock which holds the cylinders 110 and 120 in place against each other. Press-fitting the cylinders 110 and 120 against each other also acts to further compress O-ring 150. The inner wall surface 113 of cylinder 110 presses against the O-ring 150 to squeeze it into the channel 128, enhancing the compressive forces of the O-ring acting on the portion of the membrane 140 in channel 128.

The vial 102 completes the basic construction of the dialysis cell. The vial and the cylinders 110, 120 are preferably made of chemically compatible, inert plastic materials, that are preferably transparent. The vial 102 is open at the top and, in the embodiment shown, has a bottom 162 which, with wall 164, define a chamber into which the locked cylinders 110, 120 may be inserted. A downwardly extending section 166 of wall 164 acts as a base for the cell.

With the membrane cylinder 104 in place in vial 102, the seals 116 and 130 seat against the inner surface of the vial wall 164. Seal 130 acts primarily as a stabilizing member for the membrane cylinder, especially when cap 106 has been removed as discussed in more detail below. The seal 116, together with vial bottom wall 162 and membrane 140 define a first compartment 170. A second compartment 172 is defined inside the membrane cylinder 104 by the inner surface of cylinder walls 122 and the membrane 140. The compartment 172 may either be open to the ambient atmosphere, or, as shown in FIG. 6, may be covered with cap 106. Cap 106, as shown, has a rib 182 which seats in a space 184 between the walls of vial 102 and membrane cylinder 104. Rib 182 is dimensioned to fit tightly against cylinder wall section 123 and securely (but not necessarily tightly) against vial wall 164.

Prior to use, the dialysis cell is assembled by first prewashing the membrane 140 and then assembling the membrane cylinder 104 as described above. The vial 102 is then partially filled with a predetermined amount of dialysis buffer. The membrane cylinder 104 is inserted in the vial, so that seal 116 acts to confine the dialysis buffer to the compartment 170. The entire unit can then be capped with cap 106 and shipped pre-assembled and ready for use.

To begin dialysis, the user can pipette a serum sample into compartment 172 through an X-slit port in cap 106. To end dialysis, the user would normally remove the cap with the attached membrane cylinder from the vial 102.

As noted above, the cap 106 press fits over the open end 129 of membrane cylinder 104. The construction of the dialysis cell is such that when the cap is removed, e.g., upon completion of dialysis, the membrane cylinder remains attached to the cap for removal from vial 102. Subsequently, the cap can be removed from the membrane cylinder and replaced on the vial to allow for dialysate sample storage and transmittal. The top of the cap 106 advantageously contains a self-closing X-slit port to allow fluid, e.g. serum, to be added to or removed from compartment 172 with a standard pipettor without removing the cap. The standard closed-top cap may be replaced with a snap cap having an open port top. The open port allows a controlled rate of evaporation of the serum in the upper compartment during dialysis incubation. To maintain equilibrium between evaporative water loss and osmotic water gain, the size of the port must be matched to the duration and temperature of the dialysis incubation. This permits dialysis of the serum sample in the compartment 172 without dilution.

In one example, the open port in the cap had a diameter of 1.0 cm. The overall height of compartment 172 was 35 mm. Dialysis was carried out on a serum sample of 0.6 ml at room temperature for 18-20 hours. It was found the dialysate contained a negligible amount of osmotically active proteins.

Still a further feature of this invention, as shown in the embodiment of FIG. 6, is the use of magnetic stirrer beads 186 in compartment 170. The stirrer beads can be incorporated into the cell 100 during the assembly process. During dialysis, the cell may be mounted on a magnetic stirring assembly or mechanical shaking assembly to cause the beads to stir the fluid in compartment 170. In preliminary tests using glucose, stirring reduced the time to reach diffusion equilibrium from 16 hours to 2 hours.

One of the advantages of the embodiment of FIG. 6 is that the membrane 140 can be prewashed prior to assembly and then transported and stored wet. It is known that dialysis membranes require washing before use. However, their polycellulosic structure will crack and leak if they are dried. Thus, they must be transported and stored wet. The present invention, by allowing the cell to be preassembled with the dialysis buffer in place, permits the membrane to be stored wet and thus prevent cracking and leakage that would otherwise occur.

A further feature of this embodiment is that the O-ring 140 is "hidden" in sequestered channel 128 to prevent contact between the O-ring material and the serum sample. It has been found that certain O-ring materials will disturb protein binding equilibrium in sera. The present design prevents this disturbance, which can adversely alter the results and thus a diagnosis based on the dialysis results.

The dialysis cell described above is easy to use and is readily disposable after use. The unique system of seals holds the dialysis membrane in place and prevents leakage between the compartments. The magnitude of osmotic water gain is controlled by controlling the membrane surface area. Additionally, equilibrium can be established between evaporative water loss from compartment 172 and osmotic water gain through membrane 140.

Features of the invention that should be considered by the manufacturer and/or the user include the dialysis membrane pore size, dialysis membrane surface area/inner compartment volume (to optimize diffusion equilibrium), the use of materials which do not release substances that would "poison" the analytic methods employed nor adsorb free ligands and convenient access through the top with hand-held pipettors. With respect to the embodiments of FIGS. 1-5, an additional factor to be considered is a sufficiently large total cross-sectional area of slots 16 as related to the volume of the dialysis sac to allow rapid gas exchange between dissolved gases and ambient gases.

Currently known and used dialysis cells or chambers are all made of relatively costly materials. They all require assembling prior to use, disassembling after use and the insertion of a new clean piece of membrane, reassembly and then reuse. This is extremely labor-intensive, and is a principal reason why ordinary clinical laboratories are unwilling to perform such dialysis. They are not willing to go through the handicraft necessary to do the dialysis and they are not willing to concern themselves with the vagaries of tracer degradation and dialysis chemistry. The existing dialysis cells in addition, while they allow access to either the serum compartment or the buffer compartment during the course of dialysis and at the completion of dialysis, do not have large enough ports so that one can get gas equilibration from the ambient environment with the serum and the dialysate. This means that one cannot use the body's mechanism of controlling pH with a bicarbonate buffer, i.e., carbon dioxide pressure in the atmosphere.

The present invention has several advantages over known dialysis cells. First, a disposable dialysis cell is provided. The parts are easy to manufacture and assemble. In the embodiments of FIGS. 1-5, the vial 26 is widely available from laboratory equipment suppliers.

Second, one end of the dialysis chamber may be left open to the atmosphere with a sufficiently large opening so that, for the first time, a $CO_2$ environment can be used to achieve physiologic pH's employing a dialysate buffer that has the same ionic composition as serum water. Alternatively, a nonphysiologic buffer which allows for the escape of serum $CO_2$ can be used. If the assay is performed in room air, using a nonphysiologic buffer, one must employ a buffer which will turn all of the endogenous bicarbonate into carbonic acid, and one then has to allow for the carbonic acid to escape into the environment in order to get the pH back to 7.4. Undiluted serum cannot be used unless there is an opportunity for gas equilibration with the environment, either for the dissolved $CO_2$ formed by bicarbonate acid neutralization in the nonphysiologic state or by atmospheric $CO_2$ entering the serum in the physiologic state. When serum is taken out of the body, the dissolved $CO_2$ escapes into the air; the serum that sits out on the laboratory shelf has a pH of 8.5 to 9, which results in a radical pH alteration of the binding of hormones to serum proteins. Such pH's are unacceptable for equilibrium dialysis for the measurement of free hormones. In the past, this problem was overcome by diluting the serum portion, on the order of about 1 to 10 to 1 to 150 with a buffer solution and then dialyzing it against an approximately equivalent volume to a volume as much as 20 moles greater in dialysate. With such dilutions of serum, the gas exchange issue becomes effectively moot. The present invention avoids the need for diluting the serum altogether.

Another feature of the present invention resides in the ability to utilize it effectively with serum sample in either the inner or outer chamber and the buffer solution or dialysate in the other chamber. Known dialysis cells in use limit their function to placing the serum sample in the inner chamber (equivalent to the dialysis sac of this invention) and placing the buffer solution or dialysate in the outer chamber (comparable to the vial).

When a patient has ingested a drug that inhibits binding of hormones to proteins, the serum sample can be diluted. The dilution of the serum sample reduces the concentration of the inhibitor, which in turn changes the kinetics of the molecules, e.g., $T_4$, binding to serum proteins. Any dialysis naturally involves some transport of water from the buffer side into the serum side because of oncotic, osmotic pressure of the serum proteins. One way to minimize water transport is to make the serum volume large and the dialysate volume small in a practical way. The embodiments of FIGS. 1-5 accomplish this effectively and economically by allowing for placement of the serum sample in the larger volume vial and the buffer solution in the smaller volume dialysis sac. This effectively increases the pressure on the serum side to inhibit water transport. Another way to avoid the water transport problem, which is resolved by the embodiment of FIG. 6, is to provide for equilibration between water evaporation from the serum sample and water osmosis through the membrane from the buffer to the serum sample.

Another advantage to the present invention is that it allows the dialyzed buffer solution to be removed from the dialysis cell without disturbing the serum. A direct radioimmunoassay analysis can then be performed on the dialyzed buffer. Since no tracer is added to the system during dialysis, tracer deterioration is thereby avoided.

This invention can be used in many equilibrium dialysis situations for the measurement of free or unbound hormones, drugs, neuro-peptides, electrolytes, any biologically active molecule which is bound to proteins in biologic fluids or, generally, any molecular separation where it is desired to separate dialyzable molecules (e.g., salts) from non-dialyzable ones (e.g., macromolecules, such as proteins).

Among substances that can be detected using the cell of the invention are thyroxine, triiodothyronine, testosterone, cortisol, estradiol, certain anticonvulsants such as carbamazapine, valproic acid or phenyltoin, or benzodiazepines such as Valium, Librium, and the like. Of particular interest is the determination of biological substances which are bound to substance-binding proteins.

Buffers are utilized that will maintain the pH at between 7.0 and 7.8, most preferably between 7.2 and 7.6. The buffers should generally comprise salts present at normal serum ion concentration, organic acid buffers, especially organic sulfonic acid buffers, antibiotics capable of inhibiting the growth of gram-positive cocci, gram-negative bacteria, and fungi. A neutral carrier not capable of binding the biological substance being determined, such as, for example, a non-$T_4$ binding immunoglobulin, most preferably rabbit IgG, should also be present to prevent adsorption losses. A high molecular weight substance capable of binding to glass or generally to the cell dialysis walls, but incapable of binding to the biological substance being determined, such as, for example, gelatin, should be added so as to prevent nonspecific adsorption of the biological substance being determined to the walls of the dialysis cell. Additional substances such as urea, hydroxy acids or amino acids, e.g., lactic acid or glutamic acid, can also be added to the buffer composition so as to more accurately mirror physiological serum profiles.

Among organic buffers that can be utilized are:
ACES (N-2-acetamido-2-aminoethane sulfonic acid);
ADA (N-2-acetamidoaminodiacetic acid);
Bicine (N,N-bis(2-hydroxyethyl(glycine));
Bis-tris-propane (1,3-bis[tris(hydroxymethyl) methylamino]propane);
Diethylmalonic acid;
Glycineamide (glycinamide);
Glycylglycine;

HEPES (N-2-hydroxyethylpiperazine-$N^1$-2-ethanesulfonic acid);
HEPPS (N-2-hydroxyethylpiperazine-$N^1$-3-propanesulfonic acid);
Imidiazole;
MOPS (3-(N-morpholino)propanesulfonic acid);
PIPES (piperazine(N-$N^1$-bis-2-ethanesulfonic acid));
TES (2-[tris-(hydroxymethyl)methyl]aminoethanesulfonic acid));
Tetramethylammonium hydroxide;
Tricine (N-[tris(hydroxymethyl)methyl]glycine);
Triethanolamine;
TRIS (Tris(hydroxymethyl)aminomethane).

A preferred buffer will comprise potassium, calcium, magnesium and sodium ions in normal physiological concentrations of serum; chloride, phosphate and sulfate anions in normal physiological concentrations of serum; one of the aforementioned organic buffering compounds at concentrations sufficient to maintain substantial buffering capacity under the conditions desired at a range from 7.0 to 7.8, most preferably 7.2 to 7.6; an appropriate mixture of antibiotics as described previously in concentrations sufficient to substantially prevent or inhibit the growth of undesirable microorganisms; gelatin at a concentration sufficient to cover the dialysis cell wall and capable of preventing the adsorption of the biological substance being measured; and an additional neutral protein carrier such as rabbit IgG at a concentration sufficient to prevent substantial adsorption losses of the substance being determined to walls or membranes.

Specific features of the dialysis cell/buffer system for measurement of serum free thyroxine ($T_4$) are as follows:

1. Compartment volumes:

The $T_4$ RIA uses a 500 ul sample. The lower compartment is designed to hold 2.4 ml of dialysate, thus allowing for RIA in duplicate with sufficient remaining dialysate to repeat the RIA on problem samples plus allowances for pipetting losses and osmotic losses. The upper (serum) compartment has been designed to hold 0.6 ml of serum (see pH control below).

2. pH Control:

$T_4$ binding is pH dependent. The pH must be controlled in the range between 7.2 and 7.6. HEPES buffer has been chosen for pH control because its pKa at 37° C. is 7.4. HEPES anion will displace $T_4$ from binding proteins if the concentration is greater than about 60 mM. To control the pH of sera with acidosis and alkalosis, an effective HEPES concentration of 240 mM is needed. To achieve this total buffering capacity without exceeding the 60 mM anion concentration, a buffer volume 4 times the serum volume was designed. The HEPES buffer can then be distributed in a volume 5 times greater than the serum volume alone (serum=1; buffer=4), thereby reducing the serum concentration of HEPES anion to 48 mM and avoiding HEPES anion interference with $T_4$ equilibria, while maintaining the required overall buffering capacity.

3. Membrane surface area:

It was determined experimentally that the use of a 1 $cm^2$ circle of dialysis membrane provides the optimal surface area matching of diffusion equilibrium time with protein-binding equilibrium time to $T_4$ (16 hours) when the upper compartment contains 0.6 ml of serum and the lower compartment contains 2.4 ml of dialysate, and no stirring is used.

4. Dialysate protein concentrations:

To eliminate adsorbtion losses the dialysate buffer must contain protein. Gelatin and gammaglobulin do not bind $T_4$. They do interfere with the radioimmunoassay at high concentrations. In order to eliminate $T_4$ adsorbtion while maintaining gelatin and gammaglobulin concentrations below the level for interference, it was determined that neither protein alone was adequate. As a consequence, the dialysis buffer contains subthreshold concentration of both proteins in a formulation which eliminates $T_4$ adsorbtion to plastics and membranes.

5. Dialysate chemistry:

In addition to the HEPES buffer, gelatin and gammaglobulins, the remaining constituents of the dialysate buffer include the non-protein constituents in serum with concentrations of 1 mM or more to provide a virtually physiologic environment for the dialysis reaction.

6. Antibiotics:

To eliminate the possibility of bacterial growth during the dialysis incubation, a mixture of penicillin, gentamycin, streptomycin and amphotercin B is used. The concentration of each constituent is below the threshold concentration needed to alter $T_4$ binding equilibrium.

An optimized buffer for $T_4$ measurement is:
NaCl : 5265 mg/l;
DL-lactic acid : 1008 mg/l;
L-glutamic acid : 561 mg/l;
KCl : 224 mg/l;
$KH_2PO_4$ : 180 mg/l;
$CaCl_2.2H_2O$ : 275 mg/l;
$MgSO_4.7H_2O$ : 246 mg/l;
Urea : 300 mg/l;
Gelatin : 500 mg/l;
Rabbit IgG : 200 mg/l;
HEPES sodium salt : 5891 mg/l;
HEPES acid : 6046 mg/l;
Penicillin : 100000 U/l;
Streptomycin : 100 mg/l;
Amphotericin : 250 ug/l; and
Gentamycin : 100 mg/l.

The buffer is prepared in deionized water prior to use.

The present invention may be embodied in other specific forms without departing from the spirit or essential characteristics thereof. The present embodiment is presented merely as illustrative and not restrictive, with the scope of the invention being indicated by the claims rather than by the foregoing description. All changes which come within the meaning and range of equivalency of the claims are therefore intended to be embraced therein.

I claim:

1. A dialysis cell, comprising:
a vial for containing a first fluid, and having an open end portion;
a first hollow member for containing a second fluid and insertable into said open end portion of said vial, said first hollow member having a first opening at one end portion to permit open communication between the interior of the hollow member and the ambient atmosphere to allow equilibration with ambient gases, the other end portion of said hollow member having a conical shape terminating in a second opening;
a second hollow member having a conically shaped portion complementary to the conically shaped end portion of said first member, the inner diameter of said second member being greater than the other diameter of the conically shaped portion of said first member;

dialysis membrane means disposed over the second opening in said first member and extending and sandwiched between the outer surface of the conically shaped portion of said first member and the inner surface of the conically shaped portion of said second member; and sealing means disposed between said first and second members for compressing the membrane and molding to micro-channels formed in said membrane to thereby form a fluid tight seal between the membrane and said first and second members.

2. A dialysis cell according to claim 1, further comprising: means for securing said first and second members to each other to prevent separation of said members and removal of said membrane therefrom.

3. A dialysis cell according to claim 2, wherein said securing means comprises: a recess formed in one of said first and second members and a protuberance formed on the other of said first and second members for mating with said recess.

4. A dialysis cell according to claim 3, wherein said recess is formed in the outer surface of said first member and said protuberance is formed on the inner surface of said second member.

5. A dialysis cell according to claim 1, wherein said sealing means further comprises: a compressible member encircling the outer surface of said first member.

6. A dialysis cell according to claim 5, wherein said membrane is disposed between the outer surface of said first member and said compressible member.

7. A dialysis cell according to claim 5, further comprising a groove formed in the outer surface of said first member, said compressible member being disposed at least partially within said groove.

8. A dialysis cell according to claim 7, wherein said membrane is entrained in said groove between said compressible member and the outer surface of said first member.

9. A dialysis cell according to claim 1, wherein the membrane covered end portion of said first member extends beyond the end of the conically shaped end portion of said second member.

10. A dialysis cell according to claim 1, further comprising a seal member extending outwardly from the outer surface of said second member into sealing engagement with an inner wall of said vial;

wherein the membrane covered end portion of said first member extends beyond the outwardly extending seal member.

11. A membrane cylinder for use in a dialysis cell, comprising:

a first hollow member having a first opening at one end portion to permit open communication between the interior of the hollow member and the ambient atmosphere, the other end portion of said hollow member having a conical shape terminating in a second opening;

a second hollow member having a conically shaped portion complementary to the conically shaped end portion of said first member, the inner diameter of said second member being greater than the outer diameter of the conically shaped portion of said first member;

dialysis membrane means disposed over the second opening in said first member and extending and sandwiched between the outer surface of the conically shaped portion of said first member and the inner surface of the conically shaped portion of said second member; and sealing means disposed between said first and second members for compressing the membrane and molding to micro-channels formed in said membrane to thereby form a fluid tight seal between the membrane and said first and second members.

12. A membrane cylinder according to claim 11, further comprising: means for securing said first and second members to each other to prevent separation of said members and removal of said membrane therefrom.

13. A membrane cylinder according to claim 11, wherein said securing means comprises: a recess formed in one of said first and second members and a protuberance formed on the other of said first and second members for mating with said recess.

14. A membrane cylinder according to claim 13, wherein said recess is formed in the outer surface of said first member and said protuberance is formed on the inner surface of said second member.

15. A membrane cylinder according to claim 11, wherein said sealing means further comprises: a compressible member encircling the outer surface of said first member.

16. A membrane cylinder according to claim 15, wherein said membrane is disposed between the outer surface of said first member and said compressible member.

17. A membrane cylinder according to claim 15, further comprising a groove formed in the outer surface of said first member, said compressible member being disposed at least partially within said groove.

18. A membrane cylinder according to claim 17, wherein said membrane is entrained in said groove between said compressible member and the outer surface of said first member.

19. A membrane cylinder according to claim 11, wherein the membrane covered end portion of said first member extends beyond the end of the conically shaped end portion of said second member.

* * * * *

UNITED STATES PATENT AND TRADEMARK OFFICE
CERTIFICATE OF CORRECTION

PATENT NO. : 4,963,256

DATED : October 16, 1990

INVENTOR(S) : Jerald C. Nelson

It is certified that error appears in the above-identified patent and that said Letters Patent is hereby corrected as shown below:

ON TITLE PAGE of the patent, below the section identified as "U.S. PATENT DOCUMENTS", insert

--FOREIGN PATENT DOCUMENTS 291,180  9/1953  Switzerland ...........--;

Column 13, line 1, delete "other" and insert --outer-- therefor; and

Column 14, line 28, delete "11" and insert --12-- therefor.

Signed and Sealed this

Fourth Day of August, 1992

Attest:

DOUGLAS B. COMER

*Attesting Officer*  *Acting Commissioner of Patents and Trademarks*